US00PP23165P3

(12) United States Plant Patent
de Does

(10) Patent No.: US PP23,165 P3
(45) Date of Patent: Nov. 6, 2012

(54) ***THUNBERGIA* PLANT NAMED 'NEBTHU 007'**

(50) Latin Name: *Thunbergia alata*
Varietal Denomination: NEBTHU 007

(75) Inventor: Hans de Does, Muenster (DE)

(73) Assignee: Volmary GmbH, Muenster (DE)

( * ) Notice: Subject to any disclaimer, the term of this patent is extended or adjusted under 35 U.S.C. 154(b) by 5 days.

(21) Appl. No.: 12/931,597

(22) Filed: Feb. 4, 2011

(65) Prior Publication Data

US 2012/0204300 P1 Aug. 9, 2012

(51) Int. Cl.
*A01H 5/00* (2006.01)

(52) U.S. Cl. ..... Plt./226

(58) Field of Classification Search ..... Plt./263.1, Plt./226

See application file for complete search history.

*Primary Examiner* — Susan McCormick Ewoldt

(74) *Attorney, Agent, or Firm* — The Webb Law Firm

(57) ABSTRACT

'NEBTHU 007' is a new variety of *thunbergia* plant having dark velvet red/dark ochre flower colors and dark green foliage.

1 Drawing Sheet

Botanical classification: *Thunbergia alata.*
Varietal denomination: 'NEBTHU 007'.

BACKGROUND OF THE INVENTION

The present invention comprises a new and distinct cultivar of *Thunbergia alata* known by the varietal name 'NEBTHU 007'. The new variety was discovered in Muenster, Germany in the Summer of 2007. The new variety is a result of a cross of proprietary and unpatented *thunbergia* plants having breeder reference names THU 06-012 (female parent) and THU 06-23 (male parent). The purpose of the breeding program was to develop a *thunbergia* variety with improved flowers with new colors and deeper colored foliage. The new variety is similar in flower size to its female parent, but differs in flower color. 'NEBTHU 007' is similar in flower size and plant habit to its male parent, but differs in flower color and blooming time. Further, the new variety is similar in plant habit and flower size to *thunbergia* variety 'African Sunset' (unpatented), but differs in the colors of its corolla lobe, throat, and foliage. The new variety was first asexually reproduced by cuttings in September of 2007 in Muenster, Germany. The new variety has been trial and field tested and has been found to retain its distinctive characteristics and remain true to type through successive propagations.

The following characteristics have been repeatedly observed and are determined to be unique characteristics that distinguish 'NEBTHU 007' as a new and distinct cultivar from others known to the breeder:

1) Dark colored flowers that open velvet red and blush to dark ochre; and
2) Dark green foliage.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Muenster, Germany. The color readings were taken outside. The new variety was grown outside in the summertime under natural light at temperatures of 15-18° C. The new variety was 16 weeks old and grown in a 3 liter pot when described. Color references are primarily to the 2005 R.H.S. Colour Chart of The Royal Horticultural Society of London.

PLANT

Time to initiate roots: About 14 days at about 20° C.
Time to develop roots: About 30 days at about 18-20° C.
Time to produce a finished flowering plant from a rooted cutting: About 10 weeks in a 13 cm container.
Rooting habit: Shallow, with good branching.
Form: Climbing upward.
Height from media surface to top of foliage: 100 cm, reaching a final garden height of over 2 meters.
Height from media surface to top of flowers: 80 cm.
Plant diameter: 35 cm.
Vigor: Medium to strong.
Branching habit: Poor to medium.
Lateral branch:
- *Length.*—10 cm after pinching.
- *Diameter.*—0.1 cm.
- *Internode length.*—10-12 cm.
- *Strength.*—Weak.
- *Texture.*—Light pubescence present.
- *Color.*—RHS 141A.

Foliage:
- *Arrangement.*—Single.
- *Length.*—8 cm.
- *Width.*—4-5 cm.
- *Shape of leaf.*—Spear-shaped.
- *Apex.*—Acute.
- *Base.*—Bow-shaped and concave.
- *Margin.*—Spiny.
- *Texture (both surfaces).*—Light pubescence present.
- *Aspect.*—Flat, horizontal with a slight bend.

*Color*.—Young leaves: Upper surface: RHS 137A. Lower surface: RHS 139C. Mature leaves: Upper surface: RHS 137A. Lower surface: RHS 137C.

*Petiole*.—Length: 3 cm. Diameter: 0.2 cm. Texture: Light pubescence present. Color: RHS 137C.

*Veins*.—Venation type: Feather. Color Upper surface: RHS 137C. Lower surface: RHS 194A.

FLOWERS

Flower arrangement: Single.

Flower habit: Trumpet-like.

Natural flowering season: Spring until later summer (April until frost).

Fragrance: None present.

Buds (described 1 day before opening):

*Length*.—2 cm.

*Diameter*.—1.5 cm.

*Shape*.—Caudate.

*Color*.—Petals are RHS 190; calyx is RHS 141D.

Flowers:

*Diameter*.—3.5-4 cm.

*Height*.—2.5-3 cm.

Corolla:

*Arrangement*.—Base is fused to the tube.

*Petals*.—Color: Upper surface (when opening): RHS 179A. Upper surface (fully opened): RHS 179A. Lower surface (when opening): RHS 27A. Lower surface (fully opened): RHS 27A. Shape: Truncate. Length: 3.5 cm. Width: 1.5-2 cm. Apex: Truncate and slightly unrelated. Base: Fused. Margin: Smooth and slightly unrelated. Number per whorl: 5. Texture: Smooth.

*Throat color*.—RHS N77A.

*Tube color*.—RHS N77A.

Sepals:

*Appearance*.—2 spathes, like enveloping sepals.

*Length*.—2.5 cm.

*Width*.—2 cm.

*Apex*.—Obtuse.

*Base*.—Cordate.

*Margin*.—Entire.

*Texture*.—Smooth with light pubescence present.

*Color*.—RHS 145A.

Peduncles:

*Length*.—3-3.5 cm.

*Width*.—0.2 cm.

*Texture*.—Light pubescence present.

*Color*.—RHS 141D.

*Strength*.—Weak.

Disease/pest resistance: None observed to date.

Temperature tolerance: Medium; USDA Zone 11; tolerates temperatures from 5° C. to 38° C.

Drought tolerance: Regular irrigation needed.

REPRODUCTIVE ORGANS

Stamens:

*Number* (*per flower*).—4.

*Anthers*.—Shape: Didynamous, bithecous. Length: 0.5 cm. Color: RHS 4D.

*Pollen*.—Color: RHS 155A. Amount: Low.

Pistils:

*Number* (*per flower*).—1.

*Length*.—1.7 cm.

*Style*.—Length: 1.5 cm. Color: RHS 155B.

*Stigma*.—Shape: Bifid. Color: RHS 155B. Size: 0.5 cm.

*Ovaries*.—Position: Superior. Length: 0.2 cm. Width: 0.3 cm. Color: RHS 146C.

Seeds:

*Number*.—3-4.

*Length*.—0.3-0.4 cm.

*Diameter*.—0.3-0.4 cm.

*Color*.—RHS N186A.

I claim:

1. A new and distinct variety of *thunbergia* plant named 'NEBTHU 007' as is herein described and illustrated.

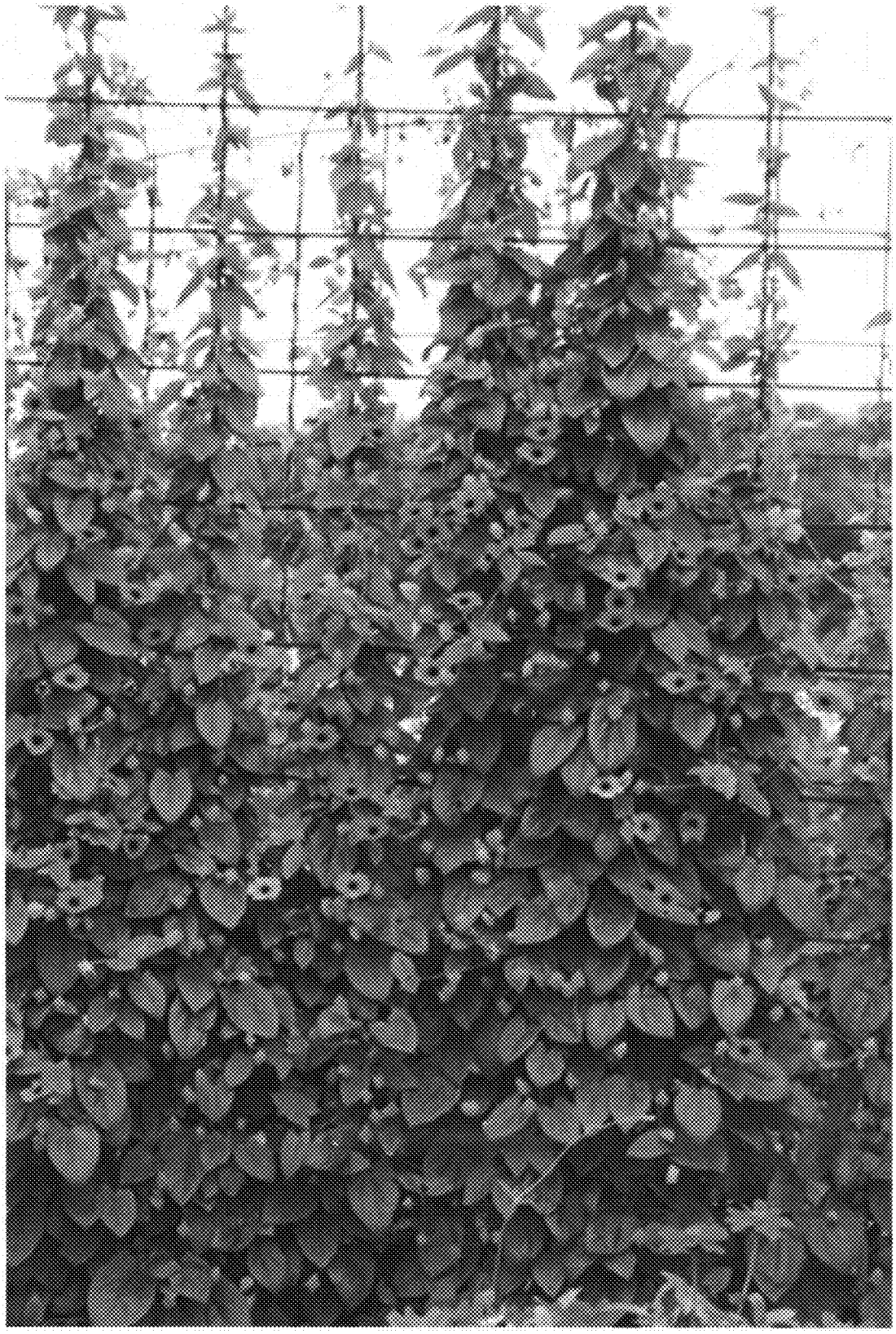

* * * * *